(12) United States Patent
Mogna et al.

(10) Patent No.: US 11,446,340 B2
(45) Date of Patent: Sep. 20, 2022

(54) PROBIOTIC BACTERIAL STRAINS AND SYMBIOTIC COMPOSITION CONTAINING THE SAME INTENDED FOR INFANT FOOD

(71) Applicant: PROBIOTICAL S.P.A., Novara (IT)

(72) Inventors: Giovanni Mogna, Novara (IT); Gian Paolo Strozzi, Novara (IT); Luca Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

(21) Appl. No.: 16/368,655

(22) Filed: Mar. 28, 2019

(65) Prior Publication Data
US 2019/0216864 A1 Jul. 18, 2019

Related U.S. Application Data

(62) Division of application No. 14/116,999, filed as application No. PCT/IB2012/000897 on May 9, 2012, now Pat. No. 10,286,017.

(30) Foreign Application Priority Data

May 9, 2011 (IT) .......................... MI2011A000793

(51) Int. Cl.
| | | |
|---|---|---|
| *A61K 35/745* | (2015.01) | |
| *A23L 33/135* | (2016.01) | |
| *C12N 1/20* | (2006.01) | |
| *A61K 35/74* | (2015.01) | |
| *C12R 1/01* | (2006.01) | |

(52) U.S. Cl.
CPC .......... *A61K 35/745* (2013.01); *A23L 33/135* (2016.08); *C12N 1/205* (2021.05); *A61K 35/74* (2013.01); *C12R 2001/01* (2021.05); *Y02A 50/30* (2018.01)

(58) Field of Classification Search
None
See application file for complete search history.

(56) References Cited

U.S. PATENT DOCUMENTS

| | | |
|---|---|---|
| 5,474,932 A | 12/1995 | Bengmark et al. |
| 6,221,404 B1 | 4/2001 | Nguyen et al. |
| 6,479,051 B1 | 11/2002 | Bruce et al. |
| 9,005,682 B2 | 4/2015 | Sprenger et al. |
| 9,883,692 B2 | 2/2018 | Hougee et al. |
| 10,028,982 B2 | 7/2018 | Mogna |
| 10,286,017 B2 | 5/2019 | Mogna et al. |

(Continued)

FOREIGN PATENT DOCUMENTS

| | | |
|---|---|---|
| BR | 112013026690 A2 | 12/2016 |
| CN | 101048168 A | 10/2007 |

(Continued)

OTHER PUBLICATIONS

Bifisterol Class IIA Medical Device for Oral Use Pamphlet/Packaging from http://www.probiotical.com. 2 pages. 2015.

(Continued)

*Primary Examiner* — Erin M. Bowers
(74) *Attorney, Agent, or Firm* — Steinfl + Bruno LLP

(57) ABSTRACT

Selection of probiotic strains belonging to the genus *Bifidobacterium* and to a symbiotic composition containing the same for use of feeding infants, is described.

12 Claims, 3 Drawing Sheets

Listeria monocytogenes ATCC 19112

(56) References Cited

U.S. PATENT DOCUMENTS

Figure 1:
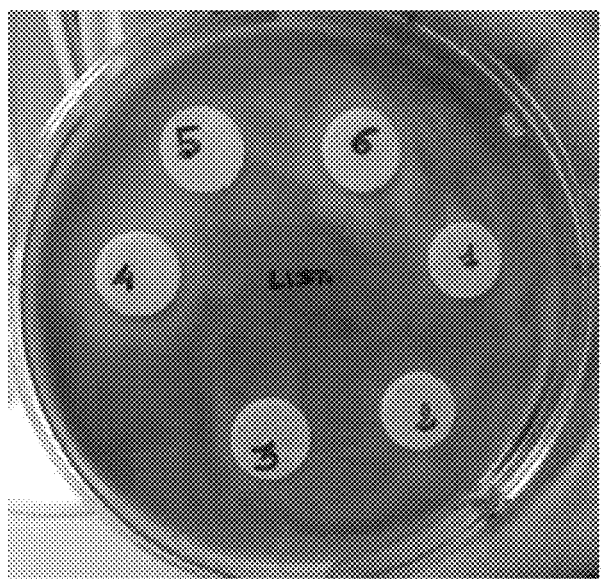

| | | |
|---|---|---|
| 10,384,847 B2 | 8/2019 | Mogna |
| 10,982,184 B2 | 4/2021 | Mogna et al. |
| 11,110,135 B2 | 9/2021 | Mogna et al. |
| 11,110,136 B2 | 9/2021 | Mogna |
| 2003/0118571 A1 | 6/2003 | Reid et al. |
| 2004/0185032 A1* | 9/2004 | Burrell .......... A61K 31/135 424/93.45 |
| 2005/0220776 A1 | 10/2005 | Brondstad et al. |
| 2007/0207132 A1 | 9/2007 | Speelmans et al. |
| 2008/0268006 A1 | 10/2008 | Molin et al. |
| 2008/0299099 A1 | 12/2008 | Heczko et al. |
| 2009/0041736 A1 | 2/2009 | Sprenger et al. |
| 2009/0180999 A1 | 7/2009 | Minatelli et al. |
| 2010/0092240 A1 | 4/2010 | Glasser |
| 2010/0168056 A1 | 7/2010 | Troup et al. |
| 2010/0278781 A1 | 11/2010 | Hougee et al. |
| 2011/0236360 A1 | 9/2011 | Ochi et al. |
| 2011/0274722 A1 | 11/2011 | Gorbach et al. |
| 2012/0058095 A1 | 3/2012 | Strozzi et al. |
| 2014/0065115 A1 | 3/2014 | Mogna et al. |
| 2014/0072543 A1 | 3/2014 | Mogna |
| 2014/0093479 A1 | 4/2014 | Mogna et al. |
| 2014/0186409 A1 | 7/2014 | Lang et al. |
| 2015/0174179 A1 | 6/2015 | Sprenger et al. |
| 2017/0049828 A1 | 2/2017 | Kim et al. |
| 2018/0236014 A1 | 8/2018 | Mogna et al. |
| 2019/0321418 A1 | 10/2019 | Mogna |
| 2020/0197447 A1 | 6/2020 | Mogna |
| 2020/0199692 A1 | 6/2020 | Mogna |
| 2020/0325440 A1 | 10/2020 | Mogna et al. |
| 2021/0023150 A1 | 1/2021 | Mogna |
| 2021/0308197 A1 | 10/2021 | Mogna |

FOREIGN PATENT DOCUMENTS

| | | |
|---|---|---|
| CN | 101432007 A | 5/2009 |
| CN | 101801220 A | 8/2010 |
| CN | 105377277 A | 3/2016 |
| EP | 2000530 A1 | 12/2008 |
| EP | 2158916 A1 | 3/2010 |
| EP | 2364712 A1 | 9/2011 |
| EP | 2455095 A1 | 5/2012 |
| EP | 2707477 B1 | 7/2018 |
| EP | 2667849 B1 | 7/2019 |
| GB | 2396811 A | 7/2004 |
| JP | H11504049 A | 4/1999 |
| JP | 2002507123 A | 3/2002 |
| JP | 2002508762 A | 3/2002 |
| JP | 2006180836 A | 7/2006 |
| JP | 2009511506 A | 3/2009 |
| JP | 2012527884 A | 11/2012 |
| JP | 2016518441 A | 6/2016 |
| KR | 2011005755 0 A | 6/2011 |
| KR | 20130038395 A | 4/2013 |
| RU | 2316586 C2 | 2/2008 |
| RU | 2354392 C1 | 5/2009 |
| RU | 2445073 C2 | 3/2012 |
| RU | 2465320 C2 | 10/2012 |
| WO | 97/29763 A1 | 8/1997 |
| WO | 00/35465 A3 | 6/2000 |
| WO | 2004/087893 A1 | 10/2004 |
| WO | 2006/082824 A1 | 8/2006 |
| WO | 2007/020884 A1 | 2/2007 |
| WO | 2007/050656 A2 | 5/2007 |
| WO | 2008/107746 A2 | 9/2008 |
| WO | 2008/153377 A1 | 12/2008 |
| WO | WO 2008/153377 * | 12/2008 |
| WO | 2010/038714 A1 | 4/2010 |
| WO | 2010/128084 A1 | 11/2010 |
| WO | 2010/133761 A1 | 11/2010 |
| WO | 2011/002168 A2 | 1/2011 |
| WO | 2011/044934 A1 | 4/2011 |
| WO | 2012/101500 A1 | 8/2012 |
| WO | 2012/123770 A1 | 9/2012 |
| WO | 2012/143787 A1 | 10/2012 |
| WO | 2012/153179 A1 | 11/2012 |
| WO | 2013/050833 A1 | 4/2013 |
| WO | 2013/093941 A2 | 6/2013 |
| WO | 2014/023995 A1 | 2/2014 |
| WO | 2014/184639 A1 | 11/2014 |
| WO | 2014/184643 A1 | 11/2014 |
| WO | 2017/163216 A1 | 9/2017 |
| WO | 2018/025204 A1 | 2/2018 |
| WO | 2018/215940 A1 | 11/2018 |

OTHER PUBLICATIONS

Bifisterol Probiotic Product Pamphlet from http://www.probiotical.com. 2 pages. 2015.

Basic Microbiology, Eighth edition. Wesley Volk and Jay Brown, eds. Addison-Wesley (1997), pp. 221, 344-345. 5 pages.

Bondarenko V. M. Molecular-cellular mechanisms of therapeutic action of probiotics. Biologicals. Prevention, diagnosis, treatment. Scientific center of expertise of medical application of the Ministry of health of the Russian Federation (Moscow) 2010 No. 1 (37) p. 31-34; 6 pages.

Botes, M., et al. "Evaluation of Enterococcus mundtii ST4SA and Lactobacillus plantarum 423 as probiotics by using a gastrointestinal model with infant milk formulations as substrate", International Journal of Food Microbiology (Dec. 2008), 128(2), 362-370. Abstract Only.

Chinese Patent Office First Office Action for Chinese Patent Application No. 201480027970.9, dated Jul. 3, 2018. 12 pages (Chinese Original + English translation).

Chinese Search Report for Chinese Application No. 201480027970.9 filed May 14, 2014 on behalf of Probiotical S.P.A. dated Jun. 21, 2018. 7 pages. (Chinese Original + English Translation).

Decision to Grant for Russian Patent Application No. 2014107771/10 filed Sep. 10, 2012 on behalf of Probiotical S.P.A. dated May 23, 2017. 11 pages (Russian original+ Partial English translation).

Del Piano et al., presented in the 7th Probiotics, Prebiotics & New Foods Meeting held in Rome on Sep. 8-10, 2013, published in Journal of Clinical Gastroenterology, 48/Suppl 1: S56-61, 2014 (Year: 2013).

Final Office Action for U.S. Appl. No. 14/116,999, filed Dec. 20, 2013 on behalf of Giovanni Mogna, dated Dec. 9, 2016. 28 pages.

Final Office Action for U.S. Appl. No. 14/116,996, filed Dec. 18, 2013 on behalf of Probiotical S.P.A. dated Jan. 25, 2019. 29 pages.

Grill, J.P., et al., "Bile Salt Toxicity to Some Bifidobacterial Strains: Role of Conjugated Bile Salt Hydrolase and pH," Canadian Journal of Microbiology, 46, pp. 878-884.Oct. 2000. 7 Pages .

International Preliminary Report on Patentability for Application No. PCT/IB2012/001848 filed Sep. 21, 2012 on behalf of Probiotical S.P.A. dated Mar. 25, 2014. 4 pages. (English Only).

International Preliminary Report on Patentability for Application No. PCT/IB2014/000731 filed May 14, 2014 on behalf of Probiotical S.P.A. dated Nov. 17, 2015. 11 pages (English Only).

International Preliminary Report on Patentability for International Application No. PCT/IB2012/000779 filed Apr. 18, 2012 on behalf of Giovanni Mogna, dated Oct. 22, 2013. 6 pages.(English Only).

International Preliminary Report on Patentability for International Application No. PCT/IB2012/001741 filed Sep. 10, 2012 on behalf of Giovanni Mogna, dated Mar. 12, 2014.10 pages.

Jackson, S.A. et al., "Improving End-User Trust in the Quality of Commercial Probiotic Products", Frontiers in Microbiology, Apr. 2019, vol. 10, Article 739, 15 pages. http://www.frontiersin.org.

Japanese Office Action for Japanese Application No. 2014-529082 filed Mar. 7, 2014 on behalf of Probiotical S.P.A. dated Jul. 19, 2016. 13 pages (Japanese Original + English Translation).

Kaewnopparat, S., et al. "In vitro probiotic properties of Lactobacillus fermentum SK5 isolated from vagina of a healthy woman", Anaerobe (Aug. 2013), 22, 6-13. 8 pages.

Klaver, F., et al., "The Assumed Assimilation of Cholesterol By Lactobacilli And *Bifidobacterial bifidum* is Due To Their Bile Salt-Deconjugating Activity," Appl Environ Microbiology,vol. 59, No. 4, pp. 1120-1124.1993. 5 Pages.

(56) References Cited

OTHER PUBLICATIONS

Lai, et al., "Lansoprazole For The Prevention of Recurrences of Ulcer Complications From Long-Term Low-Dose Aspirin Use", N Engl J Med. 346 (26) 2002: 2033-2038.
Losada, M.A., et al., "Towards A Healthier Diet for The Colon: The Influence of Fructooligosaccharides And Lactobacilli On Intestinal Health," Nutrition Research, vol. 22, pp. 71-84. 2002. 14 Pages.
Non-Final Office Action for U.S. Appl. No. 14/113,211, filed Nov. 26, 2013 on behalf of Hoffmann-Eitle SRL, dated May 29, 2019. 29 pages.
Non-Final Office Action for U.S. Appl. No. 14/116,999, filed Dec. 20, 2013 on behalf of Giovanni Mogna, dated Jun. 16, 2015. 28 pages.
Non-Final Office Action for U.S. Appl. No. 14/116,999, filed Dec. 20, 2013 on behalf of Giovanni Mogna, dated Mar. 14, 2016. 25 pages.
Non-Final Office Action for U.S. Appl. No. 14/116,999, filed Dec. 20, 2013 on behalf of Giovanni Mogna, dated Jan. 5, 2018. 26 pages.
Non-Final Office Action for U.S. Appl. No. 15/265,706, filed Sep. 14, 2016 on behalf of Probiotical S.P.A . . . dated Apr. 17, 2019. 27 pages.
Non-Final Office Action for U.S. Appl. No. 15/902,977, filed Feb. 22, 2018 on behalf of Probiotical S.P.A. dated Oct. 31, 2019. 20 pages.
Non-Final Office Action for U.S. Appl. No. 14/891,306, filed Nov. 13, 2015 on behalf of Probiotical S.P.A dated May 2, 2019 25 pages.
Notice of Allowance for U.S. Appl. No. 14/116,999, filed Dec. 20, 2013, on behalf of Probiotical S.P.A, dated Dec. 26, 2018. 14 pages.
Notice of Allowance for U.S. Appl. No. 14/116,999, filed Dec. 20, 2013, on behalf of Probiotical S.p.A, dated Sep. 4, 2018. 11 pgs.
Notice of Allowance for U.S. Appl. No. 14/346,941, filed Mar. 24, 2014 on behalf of Probiotical North America Inc., dated Apr. 8, 2019. 29 pages.
Notice of Allowance for U.S. Appl. No. 14/346,941, filed Mar. 24, 2014 on behalf of Probiotical North America Inc, dated Aug. 6, 2018. 8 pages.
Notice of Allowance for U.S. Appl. No. 14/116,996, filed Dec. 18, 2013 on behalf of Giovanni Mogna, dated Sep. 24, 2019. 16 pages.
Office Action for Japanese Patent Application No. 2016-513453 filed on behalf of Probiotical S.P.A., dated Jan. 9, 2018. 10 pages (Japanese Original + English Translation).
Office Action for Russian Patent Application No. 2015148750/15 filed May 14, 2014 on behalf of Probiotical S.P.A. dated Mar. 5, 2018. 19 pages (Russian Original + English Translation).
Ouwehand A.C., et al., "Probiotics: An Overview of Beneficial Effects," Antonie Van Leeuwenhoek, Aug. 2002, vol. 82 (1-4), 279-289. 11 pages.
Peng F., et al., "Health Education for Kidney Diseases," Hubei Science & Technology Press, Dec. 31, 2007, p. 102.(Chinese Original + English Translation) 5 pages.
Puccio G., et al., "Clinical Evaluation of a New Starter Formula for Infants Containing Live *Bifidobacterium longum* BL999 and Prebiotics," Nutrition, Jan. 2007, vol. 23 (1), 8 pages.
Restriction Requirement for U.S. Appl. No. 14/116,999, filed Dec. 20, 2013 on behalf of Giovanni Mogna, dated Mar. 11, 2015. 12 pages.
Russian Patent Office Official Action for Russian Patent Application No. 2015148752/15 filed on behalf of Probiotical S.P.A. dated Apr. 24, 2018. 11 pages (Russian original + English translation).
Russian Search Report for Russian Application No. 2015148750/15 filed on May 14, 2014 on behalf of Probiotical S.P.A. dated Mar. 5, 2018. 5 pages. (Russian original + English translation).
Russian Search Report for Russian Application No. 2015148752/15 filed on May 14, 2014 on behalf of Probiotical S.P.A. dated Apr. 20, 2018. 4 pages. (Russian original + English translation).
Scardovi V., et al., "Multiple Electrophoretic Forms of Transaldolase and 6-Phosphogluconic Dehydrogenase and Their Relationships to the Taxonomy and Ecology of the Bifidobacteria," International Journal of Systematic Bacteriology, vol. 29 (4), Oct. 1979, 312-327. 16 pages.
"The Language of Prevention" from National Public Health Partnership, 2006. Melbourne: NPHP. 9 pages.
"Study on Optimization of Exopolysaccharide and Characteristics of *Streptococcus thermophilus* ST1," 2011. 73 pages (7-8). (English Abstract).
Wang Q., et al., "Urinary Tract Infections," Shanghai Liandong Press, Jul. 31, 2001, p. 4 (original + English translation). 5 pages.
Wikipedia definition of p-value (printed on Jul. 3, 2018) 12 pages. https://en.wikipedia.org/wiki/P-value.
Wikipedia entry for "yeast", dated Mar. 1, 2011 (13 pages).
Bozzi Cionci, N., et al., "Therapeutic Microbiology: The Role of *Bifidobacterium breve* as Food Supplement for the Prevention/Treatment of Paediatric Diseases," Nutrients, 10, 1723,Published: Nov. 10, 2018. 27 Pages .
Brazilian Office Action for Brazilian Application No. BR112013028496-0 dated Oct. 17, 2019 on behalf of Probiotical S.P.A., 5 pages. Brazilian + English translation.
Brazilian Office Action for Brazilian Application No. BR112013028705-5 dated Aug. 14, 2019 on behalf of Probiotical S.P.A., 6 pages. Brazilian + English translation.
Brazilian Patent Office Official Action for Brazilian Patent Application No. BR112015027536-2 filed on behalf of Probiotical S.P.A. , dated Oct. 2, 2019 , 6 pages. (Brazilian + English translation).
Examination Report for Indian Application No. 8722/CHENP/2013 filed on behalf of Probiotical S.P.A. dated Jul. 5, 2018. 8 Pages. (Hindi + English Translation).
Final Office Action for U.S. Appl. No. 14/113,211, filed Nov. 26, 2013 on behalf of Giovanni Mogna, dated Mar. 4, 2020. 25 pages.
Hearing Notice for Indian Application No. 8722/CHENP/2013 filed on behalf of Probiotical S.P.A. dated Oct. 17, 2019. 3 Pages (Hindi+ English Translation).
Japanese Patent Office Decision To Grant for Japanese Patent Application No. 2016-513453 filed on behalf of Probiotical S.P.A , certification date Sep. 3, 2019, dated Sep. 10, 2019. 7 pages (Japanese + English translation).
Notice of Allowance for U.S. Appl. No. 14/116,996, filed Dec. 18, 2013 on behalf of Giovanni Mogna, dated May 6, 2020. 11 Pages .
Notice of Allowance for U.S. Appl. No. 14/891,306, filed Nov. 13, 2015 on behalf of Probiotical S.P.A. dated May 22, 2020 11 pages.
Notice of Allowance for U.S. Appl. No. 14/891,306, filed Nov. 13, 2015 on behalf of Probiotical S.P.A. dated Jan. 13, 2020. 15 pages.
Notice of Allowance for U.S. Appl. No. 14/116,996, filed Dec. 18, 2013 on behalf of Giovanni Mogna, dated Feb. 26, 2020. 10 Pages.
Notice of Allowance for U.S. Appl. No. 15/902,977, filed Feb. 22, 2018 on behalf of Probiotical S.P.A. dated Apr. 23, 2020. 5 Pages.
Preliminary office Action for Brazilian Application No. BR112013028709-8 filed on May 9, 2012 on behalf of Probiotical S.P.A. dated Aug. 13, 2019. 5 Pages (Portuguese and Informal English Translation).
Brazilian Office Action for Brazilian Application No. BR112013028705-5 dated Dec. 14, 2020 on behalf of Probiotical S.P.A., 8 pages. Brazilian + partial English translation.
Decision to Grant for Indian Patent No. 358118, Application No. 1949/MUMNP/2013 filed on May 9, 2012 on behalf of Probiotical S.P.A. dated Feb. 9, 2021. 28 pages.
Notice of Allowance for U.S. Appl. No. 14/891,306, filed Nov. 13, 2015 on behalf of Probiotical S.P.A. dated Jan. 15, 2021. 11 Pages.
Notice of Allowance for U.S. Appl. No. 15/902,977, filed Feb. 22, 2018 on behalf of Probiotical S.P.A. dated Jan. 25, 2021. 6 pages.
Brazilian Office Action for Brazilian Application No. BR112013028496-0 filed May 9, 2012, on behalf of Probiotical S.P.A. dated Oct. 6, 2020. Portuguese Original + English Translation. 12 pages.
Canadian Office Action for CA Application No. 2,912,013 filed on May 14, 2014 on behalf of Probiotical S.P.A. dated Aug. 24, 2020. 4 pages.
Corrected Notice of Allowability for U.S. Appl. No. 14/891,306, filed Nov. 13, 2015 on behalf of Probiotical S.P.A. dated Aug. 20, 2020. 5 pages.

(56) References Cited

OTHER PUBLICATIONS

Decision of Rejection for Chinese Application No. 201280031191. 7, dated May 12, 2020, with English translation. 14 pages.
Korean Office Action for KR Application No. 1020157035288 filed on May 14, 2014 on behalf of Probiotical S.P.A. dated Aug. 11, 2020. 8 pages (English + Original).
Notice of Allowance for U.S. Appl. No. 14/116,996, filed Dec. 18, 2013 on behalf of Giovanni Mogna, dated Dec. 3, 2020. 11 pages.
Notice of Allowance for U.S. Appl. No. 14/116,996, filed Dec. 18, 2013 on behalf of Giovanni Mogna, dated Aug. 14, 2020. 10 pages.
Notice of Allowance for U.S. Appl. No. 14/891,306, filed Nov. 13, 2015 on behalf of Probiotical S.P.A. dated Aug. 5, 2020. 9 pages.
Notice of Allowance for U.S. Appl. No. 15/902,977, filed Feb. 22, 2019 on behalf of Giovanni Mogna, dated Oct. 13, 2020 17 pages.
Notice of Allowance (Technical Examination Report) dated Sep. 14, 2020, published in Brazilian Industrial Property Journal dated Sep. 29, 2020 for Brazilian Application No. BR112013028709-8 filed on May 9, 2012 on behalf of Probiotical S.P.A. 5 pages (Portuguese + partial Eng trans.).
Amoruso, A., et al. A Systematic Evaluation of the Immunomodulatory and Functional Properties of Probiotic *Bifidobacterium breve* BR03 (DSM 16604) Lactobacillus Plantarum LP01 (LMG P-21021), Journal of Probiotics and Health, vol. 7, Issue 3, No. 214, (Dec. 27, 2019).9 pages.
CFR—Code of Federal Regulations Title 21, Part 107 "Infant Formula". 2 pages. Downloaded from The Wayback Machine, dated Feb. 22, 2011.
Corrected Notice of Allowability for U.S. Appl. No. 14/116,996, filed Dec. 18, 2013, on behalf of Giovanni Mogna, dated Mar. 1, 2021. 3 pages.
Corrected Notice of Allowability for U.S. Appl. No. 14/116,996, filed Dec. 18, 2013 on behalf of Giovanni Mogna, dated Mar. 19, 2021. 4 Pages.
Corrected Notice of Allowability for U.S. Appl. No. 14/891,306, filed Nov. 13, 2015 on behalf of Probiotical S.P.A. dated Mar. 23, 2021. 5 pages.
Non-Final Office Action for U.S. Appl. No. 14/113,211, filed Nov. 26, 2013 on behalf of Giovanni Mogna, dated Apr. 23, 2021. 26 Pages.
Notice of Allowance for U.S. Appl. No. 14/891,306, filed Nov. 13, 2015, on behalf of Probiotical S.P.A. dated May 19, 2021. 10 Pages.
Notice of Allowance for U.S. Appl. No. 15/902,977, filed Feb. 22, 2018 on behalf of Probiotical S.P.A. dated May 6, 2021. 6 Pages.
Shin et al., "Pharmacology of Proton Pump Inhibitors," *Curr Gastroenterol Rep.* Dec. 2008; 10(6): 528-534). 11 Pages.
Wikipedia, the free encyclopedia, "Infant formula". 21 pages. Downloaded from The Wayback Machine, with a date of Apr. 1, 2011.
Aragon, George et al., Probiotic Therapy for Irritable Bowel; Gastroenterology & Hepatology; United States of America ; vol. 6, Issue 1; Jan. 2010; 39-44.
Collins, M.D et al., "The phylogeny of the genus Clostridium: proposal of five new genera and eleven new species combinations", Int J Syst Bacteriol., Oct. 1994, vol. 44, No. 4: 812-26.
Database WPI Week 2011109, Thomson Scientific, London GB, for WO 2011/002168, AN: 2011-A52648, Jan. 6, 2011. 2 pages.
Database WPI Week 2011167, Thomson Scientific, London GB, for KR 2011 0057550, An: 2011-H38885, Jun. 1, 2011. 2 pages.
Final Office Action for U.S. Appl. No. 14/113,211, filed Nov. 26, 2013, on behalf of Giovanni Mogna. dated Jan. 18, 2022. 26 Pages.
Final Office Action for U.S. Appl. No. 16/322,843, filed Feb. 1, 2019 on behalf of Probiotical S.P.A. dated Oct. 13, 2021. 19 pages.
Franks, A.H et al. "Variations of bacterial populations in human feces measured by fluorescent in situ hybridization with group-specific 16S rRNA-targeted oligonucleotide probes" Appl Environ Microbiol, Sep. 1998, vol. 64, N(9), 3336-45.
Grimoud Julien, et al., "In Vitro Screening of Probiotic Lactic Acid Bacteria and Prebiotic Glucooligosaccharides to Select Effective Synbiotics," Anaerobe, Oct. 2010, vol. 16 (5), pp. 493-500. 8 pages.
Harmsen, H.J.M. "A 16S rRNA-targeted probe for detection of lactobacilli and enterococci in faecal samples by fluorescent in situ hybridization" Microb Ecol Health Dis., 1999, 11: 3-12.
International Preliminary Report on Patentability for Application No. PCT/IB2017/051710 filed Mar. 24, 2017 on behalf of Probiotical S.P.A. dated Sep. 25, 2018. 7 pages.
International Preliminary Report on Patentability for Application No. PCT/IB2017/054734 filed Aug. 2, 2017 on behalf of Probiotical S.P.A. dated Feb. 5, 2019. 7 pages.
International Preliminary Report on Patentability for International Patent Application No. PCT/IB2018/053632, dated Nov. 26, 2019. 7 pages.
International Search Report and Written Opinion, for International Application No. PCT/IB2018/053632, dated Jul. 30, 2018, 10 pages.
International Search Report and Written Opinion for International Patent Application No. PCT/IB2017/051710, dated Aug. 16, 2017. 12 pages.
International Search Report and Written Opinion for International Patent Application No. PCT/IB2017/054734, dated Nov. 13, 2017. 11 pages.
Kaur B et al., "Biomedical applications of fermenticin HV6b isolated from Lactobacillus fermentum HV6b MTCC10770." Biomed Res Int. 2013;2013:168438. doi: 10.1155/2013/168438. Epub Jul. 29, 2013. PMID: 23984320; PMCID: PMC37 45898. (Year: 2013).
Langendijk, P.S. et al. "Quantitative fluorescence in situ hybridization of Bifidobacterium spp. with genus-specific 16S rRNA-targeted probes and its application in fecal samples", App Environ Micrbiol, Aug. 1995, 61 (8): 3069-75.
Lee, Y.K et al. "Handbook of Probiotics and Prebiotics", 2nd edition (2008)—A John Wiley & Sons, Inc., Publication, p. 399. 3 pages.
Merriam Webster Definition of "Dose". 1 Page. Accessible online from https://www.merriam-webster.com/dictionary/dose.
Nett, J E et al. "Development and validation of an in vivo Candida albicans biofilm denture model." Infection and Immunity. 2010. 78(9 ): 3650-3659. (Year: 2010).
Non-Final Office Action for U.S. Appl. No. 16/087,609, filed Sep. 21, 2018 on behalf of Probiotical S.P.A. dated Feb. 27, 2020. 9 pages.
Non-Final Office Action for U.S. Appl. No. 16/322,843, filed Feb. 1, 2019 on behalf of Probiotical S.P.A. dated May 26, 2021. 26 pages.
Non-Final Office Action for U.S. Appl. No. 16/615,355, filed Nov. 20, 2019 on behalf of Probiotical S.P.A. dated Nov. 23, 2021. 13 pages.
Non-Final Office Action for U.S. Appl. No. 17/017,947, filed Oct. 15, 2020 on behalf of Probiotical S.P.A. dated Nov. 8, 2021. 28 pages.
Non-Final Office Action issued for U.S. Appl. No. 16/861,136, filed Apr. 28, 2020, on behalf of Probiotical S.P.A. dated Apr. 13, 2022. 19 Pages.
Notification of First Office Action for Chinese patent application No. 201910816928.X on behalf of Probiotical S.P.A., dated Mar. 3, 2022. Chinese with Eng transl. 14 pages.
Notification of Reexamination for Chinese Application No. CN 201280031191.7 filed Apr. 18, 2012, on behalf of Mogna Giovanni. dated Sep. 24, 2021. 18 Pages. CN Original + English Translation.
Restriction Requirement for U.S. Appl. No. 16/322,843, filed Feb. 1, 2019 on behalf of Probiotical S.P.A. dated Dec. 10, 2020. 12 pages.
Restriction Requirement for U.S. Appl. No. 16/615,355, filed Nov. 20, 2019 on behalf of Probiotical S.P.A. dated May 28, 2021. 7 pages.
Strus et al., "Studies on the effects of probiotic Lactobacillus mixture given orally on vaginal and rectal colonization and on parameters of vaginal health in women with intermediate vaginal flora," European Journal of Obstetrics & Gynecology and Reproductive Biology 163:210-215, 2012.
Vicariotto et al., "Effectiveness of the Association of 2 Probiotic Strains Formulated in a Slow Release Vaginal Product, in Women Affected by Vulvovaginal Candidiasis-A Pilot Study," J Clin. Gastroenterol. 46(1): S73-S80, 2012.

(56) References Cited

OTHER PUBLICATIONS

Wu et al., "Leaky intestine and impaired microbiome in an amyotrophic lateral sclerosis mouse model," Physiol. Rep. 3(4):e12356, 2015. (10 pages).
Yeon et al., "Fermented milk of Lactobacillus helveticus IDCC3801 reduces beta-amyloid and attenuates memory deficit," Journal of Functional Foods 2: 143-152, 2010.
Zhang et al., "Target intestinal microbiota to alleviate disease progression in amyotrophic lateral sclerosis," Clin. Ther. 39(2):322-336, 2017. (23 pages).

\* cited by examiner

PROBIOTIC BACTERIAL STRAINS AND SYMBIOTIC COMPOSITION CONTAINING THE SAME INTENDED FOR INFANT FOOD

CROSS REFERENCE TO RELATED APPLICATIONS

The present application is a divisional application of U.S. application Ser. No. 14/116,999 filed on Dec. 20, 2013 incorporated herein by reference, which, in turn, is the US national stage of International Patent Application PCT/IB2012/000897 filed on May 9, 2012 which, in turn, claims priority to Italian Patent Application MI2011A000793 filed on May 9, 2011.

The present invention relates to a selection of probiotic strains belonging to the genus *Bifidobacterium* and to a symbiotic composition containing the same and intended for infant food.

Infants fed an artificial diet show considerable differences in the composition of intestinal microbiota compared to breastfed infants; in particular, a reduction can be observed in the concentration of bifidobacteria at the expense of other potentially pathogenic microorganisms, such as *Escherichia coli* and *Clostridium* spp. The colonization of microorganisms belonging to the genus *Bifidobacterium* takes place in breastfed infants in the first 4 days after birth and bifidobacteria very soon become the prevalent microbial group. With formula feeding, on the other hand, a more heterogeneous flora composed of coliforms, bacteroides, clostridia and streptococci develops. Precisely for these reasons, formula fed infants have a higher risk of contracting intestinal infections.

In addition, an excessive production of intestinal gas seems to be the cause of so-called "colic", which afflicts numerous infants in the first months of life.

Therefore, there is a felt need to be able to obtain, in infants, the physiologically bifidogenic effect obtained through feeding with breast milk. In particular, it is desirable to be able to guarantee formula fed infants an intestinal flora such as to avoid colic.

The Applicant has provided an answer to the above-mentioned needs following an intense activity of research, at the end of which it identified a selection of bacterial strains belonging to the genus *Bifidobacterium*.

The subject matter of the present invention relates to a bacterial strain belonging to the genus *Bifidobacterium* and having the characteristics as disclosed in the appended independent claim.

The subject matter of the present invention also relates to a food composition or supplement product or pharmaceutical composition containing said bacterial strains, as disclosed in the appended independent claim. Said compositions have valid application for use in the treatment of the colic, diarrhoea and intestinal disorders, preferably in subjects in paediatric age.

Preferred embodiments of the present invention will be illustrated in the detailed description that follows.

The bacterial strains selected by the Applicant have probiotic characteristics and can be administered to infants, as they comply with specific guidelines (FAO/WHO, 2002) which require: an evaluation of the antimicrobial activity toward antagonist bacteria, the non-toxicity and non-pathogenicity of the strain, an accurate taxonomic identification thereof, adhesion to the intestinal epithelium, resistance to the gastrointestinal tract (gastric juice and bile), genetic stability, with particular reference to the transmissibility of antibiotic resistance, and desirable sensory and technological properties when used in an industrial process. Also of particular importance is the study of the cytotoxicity of the probiotics against human cells and verification of their ability to adhere to the intestinal mucosa and ability to block the adhesion of the pathogens to the intestinal cells themselves.

The Applicant selected the strains of the present invention only after having experimentally verified the above-mentioned specifications.

The bacterial strains selected by the Applicant belong to the genus *Bifidobacterium* and have an antimicrobia activity against *E. coli*. Moreover, said strains additionally have an antimicrobial activity against *Salmonella enteriditis, Clostridium difficile* and *Campylobacter jejunii*.

The selected strains belong to the species *Bifidobacterium breve* and *Bifidobacterium longum* or *Bifidobacterium longum* subsp. *longum*.

The strains selected by the Applicant are:

(i) *Bifidobacterium breve* B632, deposited by the company Probiotical SpA of Novara (Italy) with the Depositary Institution DSMZ on 7 Apr. 2011 and having the deposit number DSM 24706.

(ii) *Bifidobacterium breve* B2274, deposited by the company Probiotical SpA of Novara (Italy) with the Depositary Institution DSMZ on 7 Apr. 2011 and having the deposit number DSM 24707.

(iii) *Bifidobacterium breve* B7840, deposited by the company Probiotical SpA of Novara (Italy) with the Depositary Institution DSMZ on 7 Apr. 2011 and having the deposit number DSM 24708.

(iv) *Bifidobacterium longum* subsp. *longum* B1975, deposited by the company Probiotical SpA of Novara (Italy) with the Depositary Institution DSMZ on 7 Apr. 2011 And having the deposit number DSM 24709.

All the above strains are available and accessible to the public under the conditions established by the Budapest Treaty.

The food composition or supplement product or pharmaceutical composition of the present invention comprises a bacterial mixture which in turn comprises at least one above-mentioned bacterial strain, for use in the treatment of colic, diarrhoea and intestinal disorders, preferably in subjects in paediatric age.

In one embodiment, the bacterial mixture comprises or, alternatively, consists of strain (i) or (ii) or (iii) or (iv).

In one embodiment, the bacterial mixture comprises or, alternatively, consists of strains (i) and (ii).

In one embodiment, the bacterial mixture comprises or, alternatively, consists of strains (i) and (iii).

In one embodiment, the bacterial mixture comprises or, alternatively, consists of strains (i) and (iv).

In one embodiment, the bacterial mixture comprises or, alternatively, consists of strains (ii) and (iii).

In one embodiment, the bacterial mixture comprises or, alternatively, consists of strains (ii) and (iv).

In one embodiment, the bacterial mixture comprises or, alternatively, consists of strains (iii) and (iv).

In one embodiment, the bacterial mixture comprises or, alternatively, consists of strains (i) and (ii) and (iii).

In one embodiment, the bacterial mixture comprises or, alternatively, consists of strains (i) and (ii) and (iv).

In one embodiment, the bacterial mixture comprises or, alternatively, consists of strains (ii) and (iii) and (iv).

In one embodiment, the bacterial mixture comprises or, alternatively, consists of strains (i) and (iii) and (iv).

In one embodiment, the bacterial mixture comprises or, alternatively, consists of strains (i) and (ii) and (iii) and (iv).

Moreover, the subject matter of the present invention relates to a symbiotic composition comprising at least one of the above-mentioned probiotic bacterial strains in association with at least one prebiotic fibre. Said association advantageously enables a selective multiplication of the existing beneficial bacteria to be obtained, thus inducing advantageous local and systemic effects for the host. The symbiotic composition is intended for infants.

In particular, several "non-digestible oligosaccharides" selected from the group comprising galacto-oligosaccharides (GOS), fructo-oligosaccharides (FOS) and inulin have valid application as fibres in the context of the present invention.

A preferred embodiment relates to a composition comprising a formula for feeding infants, at least one bacterial strain of the present invention and at least one prebiotic fibre selected from among those mentioned above. Advantageously, said composition is capable of providing the infant a marked "bifidogenic" effect very similar to that of human milk.

The subject matter of the present invention relates to a bacterial strain belonging to the species *Bifidobacterium breve, Bifidobacterium longum* or *Bifidobacterium longum*, subsp. *longum*, and having an antimicrobial activity against the pathogens *E. coli, Salmonella enteriditis, Clostridium difficile* and *Campylobacter jejunii*. The pathogen *E. coli* comprises the biotype *E. coli* O157:H7. The strain that belongs to the species *Bifidobacterium breve* is selected from the group comprising or, alternatively, consisting of *Bifidobacterium breve* B632, deposited by the company Probiotical Spa of Novara (Italy) with the Depositary Institution DSMZ on 7 Apr. 2011 and having the deposit number DSM 24706; *Bifidobacterium breve* B2274, deposited by the company Probiotical SpA of Novara (Italy) with the Depositary Institution DSMZ on 7 Apr. 2011 and having the deposit number DSM 24707; *Bifidobacterium breve* B7840, deposited by the company Probiotical SpA of Novara (Italy) with the Depositary Institution DSMZ on 7 Apr. 2011 and having the deposit number DSM 24708 and *Bifidobacterium breve* BR03, deposited by the company Probiotical SpA of Novara (Italy) with the Depositary Institution DSMZ and having the deposit number DSM 16604; preferably the strain is *Bifidobacterium breve* BR03, deposited by the company Probiotical SpA of Novara (Italy) with the Depositary Institution DSMZ and having the deposit number DSM 16604. The strain that belongs to the species *Bifidobacterium longum* is *Bifidobacterium longum* subsp. *longum* B1975, deposited by the company Probiotical SpA of Novara (Italy) with the Depositary Institution DSMZ on 7 Apr. 2011 and having the deposit number DSM 24709.

The subject matter of the present invention relates to the strain *Bifidobacterium breve* B632, deposited by the company Probiotical SpA of Novara (Italy) with the Depositary Institution DSMZ on 7 Apr. 2011 and having the deposit number DSM 24706, in association with *Bifidobacterium breve* BR03, deposited by the company Probiotical SpA of Novara (Italy) with the Depositary Institution DSMZ and having the deposit number DSM 16604.

The subject matter of the present invention relates to the strain *Bifidobacterium breve* BR02, deposited by the company Probiotical SpA of Novara (Italy) with the Depositary Institution DSMZ and having the deposit number DSM 16604, in association with *Lactobacillus plantarum* LP01 deposited by the company Mofin Srl of Novara (Italy) with the Depositary Institution BCCM-LMG on 16 Oct. 2001 and having the deposit number LMG P-21021. Advantageously, the strain *Lactobacillus plantarum* LP01 shows a great activity of inhibition against pathogenic strains, as demonstrated in the experimental part that follows FIGS. 1-5).

The present invention relates to a food composition or supplement product or medical device or pharmaceutical composition comprising a bacterial mixture, said bacterial mixture comprises or, alternatively, consists of at least one bacterial strain belonging to the species *Bifidobacterium breve, Bifidobacterium longum* or *Bifidobacterium longum* subsp. *longum*, as described above, for use in the treatment of colic, diarrhoea and intestinal disorders; preferably in subjects in paediatric age. Said bacterial mixture comprises or, alternatively, consists of the strains *Bifidobacterium breve* B632 in association with *Bifidobacterium breve* BR03 or, alternatively, *Bifidobacterium breve* BR03 in association with *Lactobacillus plantarum* LP01. Said food composition or supplement product or medical device or pharmaceutical composition comprises a bacterial mixture, as described above, wherein said bacterial mixture is added or suspended or dispersed in a vegetable oil selected from among olive oil, corn oil, sunflower oil, seed oil and palm oil. Preferably it is a corn oil.

The food composition or supplement product or medical device or pharmaceutical composition can be in the form of an oily suspension or granules, powder, capsules, tablets and sachets.

The subject matter of the present invention relates to a food composition or supplement product or medical device or pharmaceutical composition as a symbiotic composition. Said symbiotic composition comprises at least one vegetable substance selected from the group comprising or, alternatively, consisting of sterols or phytosterols, stanols or phytostanols, glucomannan, konjac gum and/or at least one prebiotic fibre selected from the group comprising fructo-oligosaccharides—FOS, galacto-oligosaccharides—GOS, xylo-oligosaccharides—XOS, inulin, larch fibre or arabino-galactan and/or fermented red rice and/or betaglucans from oats, oat bran, barley, barley bran and/or aloe arborescens gel in lyophilized form. In one embodiment, said symbiotic composition comprises simethicone. In another embodiment, said symbiotic composition comprises at least one vegetable substance selected from the group comprising galacto-oligosaccharides (GOS), fructo-oligosaccharides (FOS) and inulin.

EXPERIMENTAL PART

1. Selection of the Bifidobacteria

Forty-six strains of *Bifidobacterium* spp. were studied; they were prevalently isolated from infant faeces and belong to 5 different species (*B. bifidum, B. breve, B. longum* subsp. *infantis, B. longum* subsp. *longum, B. adolescentis* and *B. pseudocatenulatum*). The microorganisms considered are part of the BUSCoB collection (Bologna University Scardovi Collection of Bifidobacteria, University of Bologna, Italy) present at the DiSTA.

2. Selection of the Target Pathogenic Microorganisms

Various strains of *Escherichia coli* were taken into consideration: 1 strain of *E. coli* from a collection (ATCC 11105), 1 strain of *E. coli* isolated from faeces during a urinary tract infection (strain M85), which had demonstrated to be a good target microorganism in previous studies, and two strains of *E. coli* isolated from infants affected by colic (strain GC6a and GC23a). *E. coli* is a major etiological agent of acute diarrhoea in children. Furthermore, an examination was made of a strain of *Salmonella enteriditis*, the main microorganism responsible for diarrhoeas of bacterial origin in children in Italy (Infante Pina et al., 2008); a strain of *Clostridium difficile*, a major etiological agent of acute diarrhoea in children (Infante Pina et al., 2008); and a strain of *Campylobacter jejuni*, which is likewise a cause of acute diarrhoea in children (Infante Pina et al., 2008).

3. Study of the Antimicrobial Activity of the Selected Microorganisms

All 46 microorganisms were analyzed for their ability to inhibit the growth of *E. coli* ATCC 11105™, M85, GC 6a, GC 23a and *S. enteriditis* M94. A preliminary screening for antimicrobial activity was performed using the "spot agar test", according to the protocol briefly summarized here.

SPOT AGAR TEST: use is made of an overnight (o.n.) culture of each strain of *Bifidobacterium*, having an absorbance at 600 nm ($A_{600}$) of about 0.7-1, corresponding to a full exponential phase. A TPY-agar plate is used; the plate is divided into 4 and each quadrant is inoculated with 10 ηl of the o.n. culture of each strain. The plate is incubated 24 h at 37° C. under anaerobiosis. Once growth has occurred, the surface is covered with a 7-8 ml layer of soft agar medium for *E. coli* (NH+0.7% agar), inoculated with 100 ηl of an o.n. culture of the marker strain. The plate is incubated under conditions allowing the growth of the marker strain. After 24-48 hours of incubation, depending on the marker strain used, the presence of an inhibition halo can be observed around the inoculum of each strain of *Bifidobacterium*. This halo is measured with a ruler. The test is repeated at least twice. The results obtained—the average of two experiments—are shown in Table 1. Table 1 shows the inhibition halos produced by the 5 marker strains for only 16 of the 46 strains tested.

TABLE 1

| Strain | E. coli ATTC 11105 | E. coli M85 | E. coli. GC 6a | E. coli GC 23a | S. enteriditis M94 |
|---|---|---|---|---|---|
| B 2274 | 0.8 | 0.8 | 1 | 1 | 1.3 |
| B 632 | 1.2 | 1.2 | 0.8 | 0.9 | 1.2 |
| B 1975 | 0.9 | 0.7 | 0.7 | 0.6 | 1.2 |
| B7840 | 0.7 | 0.7 | 1 | 0.6 | 1 |
| B 2091 | 0.4 | 0.3 | 0.6 | 0.6 | 0.7 |
| B 2021 | 0.6 | 0.6 | 0.9 | 0.9 | 1 |
| B 2150 | 0.6 | 0.6 | 1 | 0.8 | 1 |
| B 2195 | 0.5 | 0.7 | 0.9 | 0.7 | 1.1 |
| Re 12 | 0.9 | 0.6 | 0.8 | 0.8 | 1 |
| B2101 | 0.9 | 1 | 0.9 | 1 | 1 |
| B 8452 | 0.5 | 0.6 | 0.1 | 0.4 | 0.2 |
| B 2192 | 0.9 | 0.7 | 1 | 0.7 | 1.5 |
| B 2055 | 0.7 | 0.9 | 0.3 | 0.5 | 0.5 |
| B 7958 | 0.7 | 0.7 | 0.6 | 0.8 | 1.1 |
| B 7947 | 0.7 | 0.7 | 0.4 | 0.3 | 0.5 |
| B1412 | 1.2 | 1.2 | 1.3 | 0.9 | 1 |

As can be noted from an examination of Table 1, this study revealed the presence of strains with a good antagonistic activity above all against the two strains of *E. coli* isolated from infants with colic and *Salmonella enteriditis*. Only the strains which globally exhibited inhibition haloes of larger size were selected.

The antagonistic activity of the 16 selected strains against *Clostridium difficile* M216 and *Campylobacter jejuni* LMG8841 was then assessed. The results obtained—the average of two experiments—are presented in Table 2.

TABLE 2

Size of the inhibition haloes (in cm) produced by *Clostridium difficile* M216 and *Campylobacter jejuni* LMG8841 for the 16 selected *Bifidobacterium* strains.

| Strain | C. jejuni LMG8841 | C. difficile M216 |
|---|---|---|
| B2091 | 0.8 | 0.4 |
| B2274 | 1 | 0.5 |
| B2021 | 1 | 0.4 |
| B 632 | 0.8 | 0.5 |
| B2150 | 0.8 | 0.4 |
| B2195 | 1.2 | 0.5 |
| B1412 | 1.1 | 0.5 |
| Re 12 | 1.1 | 0.4 |
| B2101 | 0.8 | 0 |
| B1975 | 0.8 | 0.5 |
| B8452 | 0.8 | 0.4 |
| B2192 | 1 | 0.4 |
| B2055 | 1 | 0.3 |
| B7958 | 1.1 | 0.4 |
| B7947 | 0.3 | 0.3 |
| B7840 | 1.4 | 0.3 |

The results obtained revealed a high inhibitory activity toward *C. jejuni* LMG8846 and a weaker—though distinctly present in the majority of the strains—activity against *C. difficile* M216.

An assessment was then made of the antimicrobial power of the supernatant obtained from o.n. cultures of the 16 selected microorganisms toward two strains isolated from infants affected by colic and toward *S. enteriditis*. The supernatant, having a pH comprised in the interval 5.5-6.2, was brought to pH 6.5 before the test was performed. The assay was performed using two methods briefly described here: "well diffusion assay" and "blank disk test".

WELL DIFFUSION ASSAY: use is made of an overnight (o.n.) culture of each strain of *Bifidobacterium*, having an $A_{600}$ of about 0.7-1, corresponding to a full exponential phase. The culture is centrifuged at 10000 rpm for 30 minutes; the supernatant is re-centrifuged at 14000 rpm for 15 minutes and immediately re-centrifuged. It is then brought to pH 6.5 with NaOH 1N. A layer of soft agar inoculated with 500 ηL of a suspension of *E. coli* $10^6$ CFU/ml (or of any other marker strain used) is applied on a plate. After the agar has solidified, wells are prepared with a sterile Pasteur pipette and 50-80 ηl of neutralized supernatant of *Bifidobacterium* spp. is introduced into the wells. The plate is incubated o.n. at 37° C. under conditions allowing the growth of the marker strain (37° C. under aerobiosis for *E. coli*).

BLANK DISK METHOD: Centrifugation of the *Bifidobacterium* culture and neutralization of the supernatant were carried out as above. Use is made of a Nutrient Agar (NA) plate in the case of *E. coli* or other media if different strains are used. The marker strain is inoculated onto the surface starting from a suspension having a cellular concentration of $10^6$ CPU/ml. A disk (previously sterilized) having a diameter of one or is soaked with 0.1 ml of supernatant (both neutralized and non-neutralized) and is rested upon the plate. The plate is incubated under conditions suitable tor the growth of the marker strain.

The inhibitory effect of the microorganisms on the marker microorganisms as revealed by the spot agar test seems to be due mainly, but not only, to the production of acidic metabolites which, by lowering the pH of the surrounding environment, bring about an inhibition of the pathogens. However, the production of bacteriocins seems possible.

Nevertheless, in order to better characterize the antimicrobial activity of the supernatant of the microorganisms used in this study, an assessment was made of the growth kinetics of some marker strains (*E. coli* ATCC11105™, *S. enteriditis* M94, *E. coli* GC 6a and *E. coli* GC 23a) in the presence of known amounts of the supernatant of each strain of *Bifidobacterium*. The marker strain was inoculated into the NB (Nutrient Broth) medium with no addition (this represents the control) and in the presence of known amounts of supernatant derived from an o.n. culture of *Bifidobacterium* spp. The supernatant was used both as such and after neutralization at three different concentrations: 12.5% (v/v), 25% (v/v) and 50% (v/v). At defined intervals of time a measurement was made of the $A_{620}$ of the marker strain, indicative of the microorganism's growth. The highest concentration of supernatant was eliminated after the first attempts, because it completely impeded the growth of the marker microorganism.

The data obtained confirm the conclusions set forth above.

4. Determination of the Sensitivity or Resistance of the Selected Bifidobacteria to Different Antibiotics and Determination of the Minimal Inhibitory Concentration (MIC)

Antibiotic sensitivity or resistance testing is one of the basic studies for evaluating the possibility of using a microorganism in in vivo tests. It is important for the microorganism to be as sensitive as possible to the main antibiotics used in therapy in order to avoid the risk of transmitting antibiotic resistance to other intestinal microorganisms; on the other hand, probiotics are often jointly administered with an antibiotic therapy and hence antibiotic resistance becomes a fundamental requisite for co-administration (Ouba et al, 2008). In this study, 10 antibiotics traditionally used to evaluate antibiotic resistance in probiotic strains (ampicillin, chloramphenicol, erythromycin, tetracycline, vancomycin, kanamycin, streptomycin, trimethoprim, cefuroxime and gentamycin) were taken into consideration; they were tested in a concentration interval of 2-1024 μg/ml. Furthermore, the MIC of another three antibiotics commonly used in neonatal therapy (amoxicillin, ceftriaxone and clarithromycin), tested at the same concentrations, was determined. The MIC was evaluated by analyzing the growth of the selected Bifidobacteria in the presence of increasing antibiotic concentrations; growth was evaluated by measuring the $A_{620}$. The resistance or sensitivity to antibiotics was evaluated using the guidelines published by the European Commission (EU commission, 2002) and the European Food Safety Authority (EFSA, 2005).

The results obtained indicate that the selected strains show resistance to ampicillin, kanamycin and amoxicillin, whereas, in general, many of the tested strains showed to be sensitive to the other antibiotics taken in consideration.

The results obtained enabled the selection of the 4 strains of *Bifidobacterium* spp., to which the present invention relates, since they exhibit antimicrobial activity against different strains of *E. coli* (gas-producing bacteria present in higher concentrations in infants that suffer from colic than in infants that do not). Moreover, said strains show an interesting antimicrobial activity against bacteria that are most frequently the cause of diarrhoea of bacterial origin in infants (*Salmonella enteriditis, Clostridium difficile* and *Campylobacter jejunii*) as well as resistance to only a limited number of antibiotics. None of the 4 selected strains demonstrated to be capable of transferring the genes for antibiotic resistance to Bifidibacteria or Lactobacilli, even in the cases where the genes were identified via PCR in the chromosomal DNA of the Bifidobacteria.

5. Method for Testing Inhibition on Plates

Bacteria with Inhibiting Action
a. The bacterium whose inhibitory activity against faecal bacteria it is intended to verify of undergoes at least two sequential transplants in MRS broth medium (test tubes containing 15 ml).
  i. If the bacterium belongs to the genus *Bifidobacterium*, the MRS broth will be supplemented with 1% Cysteine Chlorohydrate (5% sol.).
b. The fresh broth culture (cultured 22+/−2 hours) is centrifuged and the cells are washed once in sterile water.
c. The cells are then centrifuged and resuspended in 5 ml of fresh MRS broth medium.
2. Sensitive Faecal Bacterium
a. The bacterium to be subjected to inhibition undergoes at leant two sequential transplants in MacConkey broth medium (test tubes containing 10 ml).
b. The fresh broth culture is diluted in water so as to obtain an optical density of 0.600-0.700 at a wavelength of 600 nm.
c. 100 ml of this bacterial suspension is applied on a MacConkey agar plate and evenly distributed over the entire surface using a suitable sterile spatula until the liquid has been completely absorbed.
3. An 11 mm diameter paper disk (antibiogram disk) is placed on the surface of the plate, which is made to absorb 100 ml of the bacterial suspension of the strain to be tested (see step 1-c).
4. The plate is incubated in a thermostat at 37° C. for 24 hours.

Results: if the bacterium is inhibiting, a halo indicating no growth will be visible around the disk. The dimensions of the halo will be proportionate to the capability of the strain to produce substances with a bacteriostatic/bactericidal action that spread through the agar.

6. Inhibition Tests on Plates

For each potentially inhibiting probiotic, a culture is prepared and incubated for 24 hours in MRS broth. The cells are then washed and resuspended in fresh MRS broth medium. A fresh broth culture of the pathogenic bacterium is evenly spread on the surface of plates containing the agarized medium, specific for the pathogenic species it is intended to inhibit, in an amount of 100 l per plate of the first decimal dilution. The cells thus treated are adsorbed onto a paper disk, in an amount of 100 l per disk. After incubation at 37° C. for 24 hours a measurement is made of the inhibition halo, represented by the area extending between the edge of the disk and the edge of growth of the tested pathogen.

The tests of the inhibition activity of the six probiotics against the five pathogens are listed and represented below. The results are reported as inhibition haloes expressed in millimetres.

6.1 For *Listeria monocytogenes* ATCC 19112, the results are given in FIG. 1.
FIG. 1 shows:
Probiotic strains mm:
1. *L. reuteri* DLLRE08, DSM 25684 0 mm
2. *L. reuteri* ID 1774 LRE 02, DSM 23878 0 mm 3. *L. reuteri* DSM 17938 (Positive ref.) 0 mm
4. *L. plantarum* LP01 LMG P-21021 5 mm
5. *L. delbr.* susp. *bulgaricus* LDD01 2 mm
6. *L. pentosus* PCB 101 4 mm 6.2 For *Enterecoccus* sp. (from infant faeces), the results are given in FIG. 2.

Figure 2:
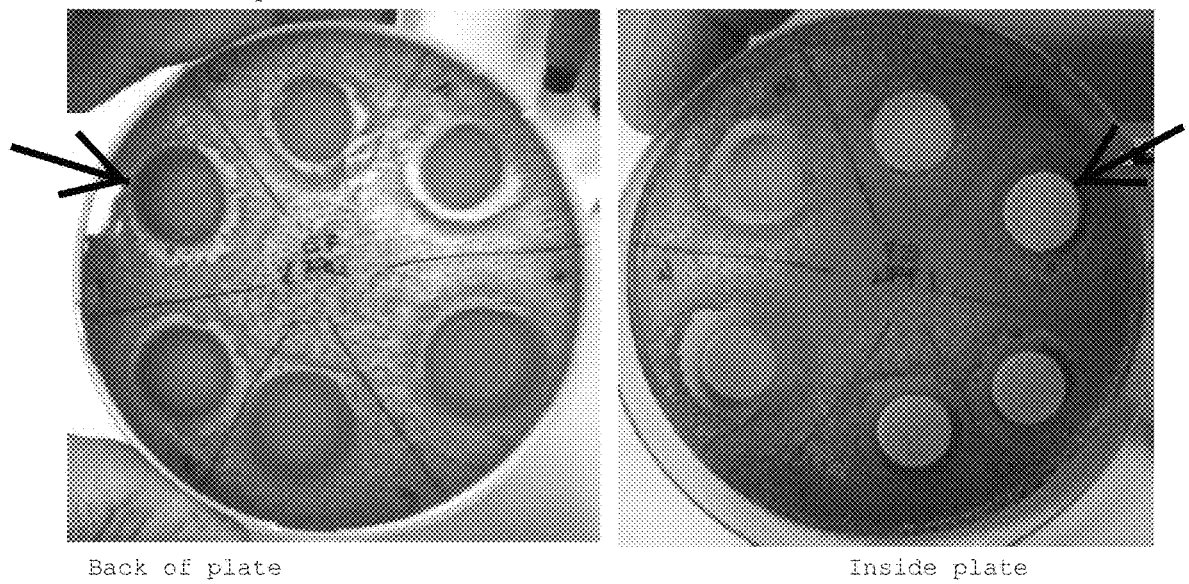

FIG. 2 shows (in a clockwise direction, starting from the arrow—back of plate):
Probiotic strains mm:
1. *L. reuteri* DLLRE08, DSM 25684
2. *L. reuteri* ID 1774 LRE 02, DSM 23878
3. *L. reuteri* DSM 17938 (Positive ref.)
4. *L. plantarum* LP01 LMG P-21021
5. *L. delbr.* susp. *bulgaricus* LDD01
6. *L. pentosus* PCB 101

FIG. 2 shows (in a clockwise direction, starting from the arrow—inside plate):
Probiotic strains mm:
1. *L. reuteri* DLLRE08, DSM 25684
2. *L. reuteri* ID 1774 LRE 02, DSM 23878
3. *L. reuteri* DSM 17938 (Positive ref.)
4. *L. plantarum* LP01 LMG P-21021
5. *L. delbr.* susp. *bulgaricus* LDD01
6. *L. pentosus* PCB 101
Results: Inhibition haloes expressed in millimetres.
Probiotic strains mm:
1. *L. reuteri* DLLRE08, DSM 25684 3 mm
2. *L. reuteri* ID 1774 LRE 02, DSM 23878 3 mm
3. *L. reuteri* DSM 17938 (Positive ref.) 3 mm
4. *L. plantarum* LP01 LMG P-21021 5 mm
5. *L. delbr.* susp. *bulgaricus* LDD01 4 mm
6. *L. pentosus* PCB 101 2 mm 6.3 For *Escherichia coli* ATCC 8739, the results are given in FIG. 3.

Figure 3:
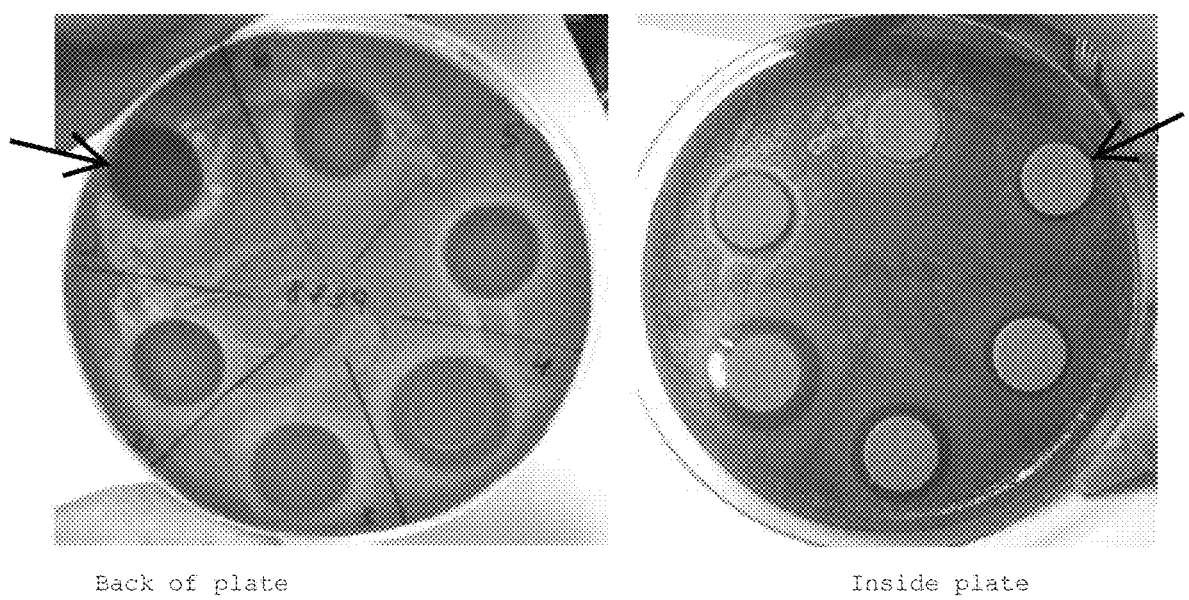

FIG. 3 shows (in a clockwise direction, starting from the arrow—back of plate):
Probiotic strains mm:
1. *L. reuteri* DLLRE08, DSM 25684
2. *L. reuteri* ID 1774 LRE 02, DSM 23878
3. *L. reuteri* DSM 17938 (Positive ref.)
4. *L. plantarum* LP01 LMG P-21021
5. *L. delbr.* susp. *bulgaricus* LDD01
6. *L. pentosus* PCB 101

FIG. 3 shows (in a clockwise direction, starting from the arrow—inside plate):
Probiotic strains mm:
1. *L. reuteri* DLLRE03, DSM 25684
2. *L. reuteri* ID 1774 LRE 02, DSM 23878
3. *L. reuteri* DSM 17938 (Positive ref.)
4. *L. plantarum* LP01 LMG P-21021
5. *L. delbr.* susp. *bulgaricus* LDD01
6. *L. pentosus* PCB 101
Results: Inhibition haloes expressed in millimetres
Probiotic strains mm:
1. *L. reuteri* DLLRE08, DSM 25684 0 mm
2. *L. reuteri* ID 1774 LRE 02, DSM 23878 1 mm
3. *L. reuteri* DSM 17938 (Positive ref.) 2 mm
4. *L. plantarum* LP01 LMG P-21021 4 mm
5. *L. delbr.* susp. *bulgaricus* LDD01 2 mm
6. *L. pentosus* PCB 101 1 mm 6.4 For *Escherichia coli* ATCC 35218, the results are given in FIG. 4.

Figure 4:
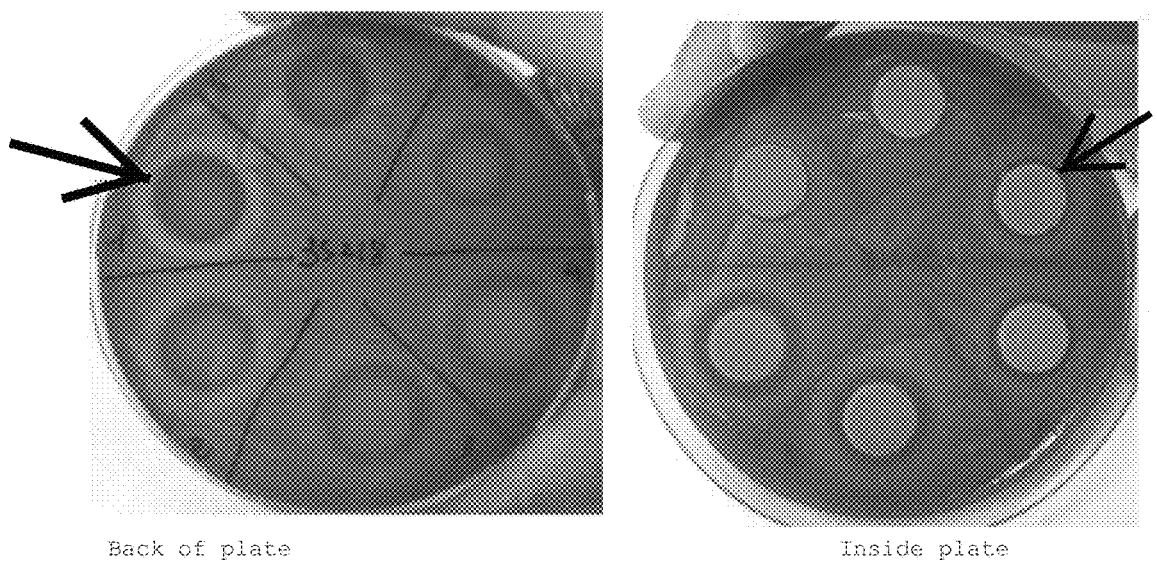

FIG. 4 shows (in a clockwise direction, starting from the arrow—back of plate):
Probiotic strains mm:
1. *L. reuteri* DLLRE08, DSM 25684
2. *L. reuteri* ID 1774 LRE 02, DSM 23878
3. *L. reuteri* DSM 17938 (Positive ref.)
4. *L. plantarum* LP01 LMG P-21021
5. *L. delbr.* susp. *bulgaricus* LDD01
6. *L. pentosus* PCB 101

FIG. 4 shows (in a clockwise direction, starting from the arrow—inside plate):
Probiotic strains mm:
1. *L. reuteri* DLLRE08, DSM 25684
2. *L. reuteri* ID 1774 LRE 02, DSM 23878
3. *L. reuteri* DSM 17938 (Positive ref.)
4. *L. plantarum* LP01 LMG P-21021
5. *L. delbr.* susp. *bulgaricus* LDD01
6. *L. pentosus* PCB 101
Results: Inhibition haloes expressed in millimetres
Probiotic strains mm:
1. *L. reuteri* DLLRE08, DSM 25684 4 mm
2. *L. reuteri* ID 1774 LRE 02, DSM 23878 2 mm
3. *L. reuteri* DSM 17938 (Positive ref.) 5 mm
4. *L. plantarum* LP01 LMG P-21021 5 mm
5. *L. delbr.* susp. *bulgaricus* LDD01 2 mm
6. *L. pentosus* PCB 101 1 mm 6.5 For *Klebsiella* sp (from infant faeces), the results are given in FIG. 5.

Figure 5:
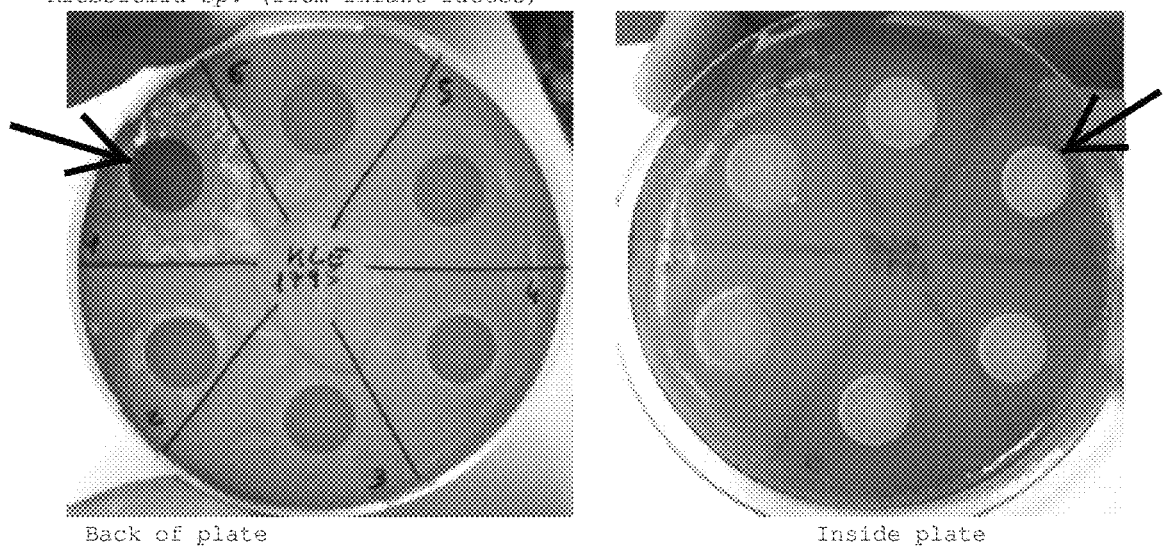

FIG. 5 shows (in a clockwise direction, starting from the arrow—back of plate):
Probiotic strains mm:
1. *L. reuteri* DLLRE08, DSM 25684
2. *L. reuteri* ID 1774 LRE 02, DSM 23878
3. *L. reuteri* DSM 17938 (Positive ref.)
4. *L. plantarum* LP01 LMG P-21021
5. *L. delbr.* susp. *bulgaricus* LDD01
6. *L. pentosus* PCB 101

FIG. 5 shows (in a clockwise direction, smarting from the arrow—inside plate):
Probiotic strains mm:
1. *L. reuteri* DLLRE08, DSM 25684
2. *L. reuteri* ID 1774 LRE 02, DSM 23878
3. *L. reuteri* DSM 17938 (Positive ref.)
4. *L. plantarum* LP01 LMG P-21021
5. *L. delbr.* susp. *bulgaricus* LDD01
6. *L. pentosus* PCB 101
Results: inhibition haloes expressed in millimetres
Probiotic strains mm:
1. *L. reuteri* DLLRE08, DSM 25684 0 mm
2. *L. reuteri* ID 1774 LRE 02, DSM 23878 2 mm
3. *L. reuteri* DSM 17938 (Positive ref.) 2 mm
4. *L. plantarum* LP01 LMG P-21021 3 mm
5. *L. delbr.* susp. *bulgaricus* LDD01 1 mm
6. *L. pentosus* PCB 101 0 mm

The invention claimed is:

1. A formula for feeding infants, comprising
  a bacterial mixture comprising *Bifidobacterium breve* B632, deposited by the company Probiotical SpA of Novara (Italy) with the Depositary Institution DSMZ on 07.04.2011 and having the deposit number DSM 24706; alone or in combination with
  at least one bacterial strain belonging to the species *Bifidobacterium breve*, *Bifidobacterium longum* or *Bifidobacterium longum* subsp. *longum* and having an antimicrobial activity against the pathogens *E. coli*, *Salmonella enteriditis*, *Clostridium difficile* and *Campylobacter jejunii* and
  at least one prebiotic fibre.

2. The formula for feeding infants according to claim 1, wherein said bacterial mixture is added or suspended or dispersed in a vegetable oil selected from olive oil, corn oil, sunflower oil, seed oil and palm oil.

3. The formula for feeding infants according to claim 1, wherein said formula for feeding infants is a symbiotic composition comprising at least one vegetable substance selected from the group comprising of sterols or phytosterols, stanols or phytostanols, glucomannan, konjac gum and/or at least one prebiotic fibre selected from the group comprising fructo-oligosaccharides FOS, galacto-oligosaccharides—GOS, xylo-oligosaccharides—XOS, inulin, larch fibre or arabinogalactan and/or fermented red rice and/or betaglucans from oats, oat bran, barley, barley bran and/or aloe arborescens gel in lyophilized form.

4. The formula for feeding infants according to claim 1, wherein said formula for feeding infants comprises simethicone.

5. The formula for feeding infants according to claim 3, wherein said at least one vegetable substance is selected from the group comprising galacto-oligosaccharides (GOS), fructo-oligosaccharides (FOS) and inulin.

6. The formula for feeding infants according to claim 1, wherein said bacterial mixture comprises a strain selected from the group consisting of
Bifidobacterium breve B2274, deposited by the company Probiotical SpA of Novara (Italy) with the Depositary Institution DSMZ on 07.04.2011 and having the deposit number DSM 24707; and
Bifidobacterium breve B7840, deposited by the company Probiotical SpA of Novara, (Italy) with the Depositary Institution DSMZ on 07.04.2011 and having the deposit number DSM 24708.

7. The formula for feeding infants according to claim 1, wherein said bacterial mixture further comprises Bifidobacterium longum subsp. longum B1975 deposited by the company Probiotical SpA of Novara (Italy) with the Depositary Institution DSMZ on 07.04.2011 and having the deposit number DSM 24709.

8. The formula for feeding infants according to claim 1, wherein said bacterial mixture further comprises Lactobacillus plantarum LP01 deposited by the company Mofin Srl of Novara (Italy) with the Depositary Institution BCCM-LMG on 16.10.2001 and having the deposit number LMG P-21021.

9. The formula for feeding infants of claim 1, wherein said bacterial mixture comprises
Bifidobacterium breve B632, deposited by the company Probiotical SpA of Novara (Italy) with the Depositary Institution DSMZ on 07.04.2011 and having the deposit number DSM 24706 and
Bifidobacterium breve BR03, deposited by the company Probiotical SpA of Novara (Italy) with the Depositary Institution DSMZ and having the deposit number DSM 16604.

10. The formula for feeding infants of claim 1, wherein the at least one prebiotic fibre is selected from the group consisting of galacto-oligosaccharides (GOS), fructooligosaccharides (FOS) and inulin.

11. The formula for feeding infants of claim 1, wherein said bacterial mixture comprises strain Bifidobacterium breve BR03 deposited by the company Probiotical SpA of Novara (Italy) with the Depositary Institution DSMZ and having the deposit number DSM 16604.

12. The formula for feeding infants of claim 1, wherein said bacterial mixture comprises Bifidobacterium breve strains
Bifidobacterium breve B2274 deposited by the company Probiotical SpA of Novara (Italy) with the Depositary Institution DSMZ on 07.04.2011 and having the deposit number DSM 24707;
Bifidobacterium breve B7840 deposited by the company Probiotical SpA of Novara, (Italy) with the Depositary Institution DSMZ on 07.04.2011 and having the deposit number DSM 24708; and
Bifidobacterium breve BR03 deposited by the company Probiotical SpA of Novara (Italy) with the Depositary Institution DSMZ and having the deposit number DSM 16604.

* * * * *